United States Patent [19]

Brunelle et al.

[11] Patent Number: 4,904,810
[45] Date of Patent: * Feb. 27, 1990

[54] BISCHOLOROFORMATE PREPARATION METHOD WITH PHOSGENE REMOVAL AND MONOCHLOROFORMATE CONVERSION

[75] Inventors: Daniel J. Brunelle, Scotia, N.Y.; Thomas G. Shannon, Evansville, Ind.

[73] Assignee: General Electric Company, Schenectady, N.Y.

[ * ] Notice: The portion of the term of this patent subsequent to Feb. 20, 2004 has been disclaimed.

[21] Appl. No.: 224,528

[22] Filed: Jul. 25, 1988

Related U.S. Application Data

[63] Continuation-in-part of Ser. No. 4,386, Jan. 16, 1987, abandoned.

[51] Int. Cl.$^4$ .................... C07C 68/02; C07C 69/96
[52] U.S. Cl. .................... 558/281; 544/347; 549/16; 549/54; 549/308; 549/359; 549/466; 548/440

[58] Field of Search .................... 558/281; 548/440; 549/308, 359, 16, 466, 54; 544/347

[56] References Cited

U.S. PATENT DOCUMENTS 4,638,077  1/1987  Brunelle et al. .................... 558/281

Primary Examiner—Vivian Garner
Attorney, Agent, or Firm—William H. Pittman; James C. Davis, Jr.

[57] ABSTRACT

Aqueous bischloroformates are prepared by the reaction of a dihydroxyaromatic compound (e.g., bisphenol A) with phosgene in a substantially inert organic liquid (e.g., methylene chloride) and in the presence of an aqueous alkali metal or alkaline earth metal base, at a pH below about 8. After all solid dihydroxyaromatic compound has been consumed, the pH is raised to a higher value in the range of about 7–12, preferably 9–11, and maintained in said range until a major proportion of the unreacted phosgene has been hydrolyzed. At the same time, any monochloroformate in the product may be converted to bischloroformate.

12 Claims, No Drawings

BISCHOLOROFORMATE PREPARATION METHOD WITH PHOSGENE REMOVAL AND MONOCHLOROFORMATE CONVERSION

This application is a continuation-in-part of copending application Ser. No. 4,386, filed Jan. 16, 1987, now abandoned.

This invention relates to the preparation of aromatic bischloroformate compositions, and more particularly to the disposal of unreacted phosgene at the completion of such preparation.

Aromatic bischloroformate compositions are useful in the preparation of polycarbonates, both as linear high polymers and as cyclic polycarbonate oligomers. The latter are in turn known to be useful for the preparation of linear polycarbonates of very high molecular weight.

Many methods for aromatic bischloroformate preparation involve the reaction of a salt of a dihydroxyaromatic compound, especially a bisphenol, with phosgene. In order to ensure complete conversion of the dihydroxyaromatic compound to its salt, such reactions normally take place at relatively high pH levels. For example, U.S. Pat. Nos. 3,959,335 and 3,966,785 disclose reactions of this type at a pH of 9–12 and 12 or higher, respectively.

Under such conditions, a large excess of phosgene, typically about 2.5–5.0 moles per mole of dihydroxyaromatic compound, is required for substantially complete conversion. The use of phosgene in these proportions is wasteful. It has been discovered that one factor in the large amount of phosgene consumed in such methods is that hydrolysis of phosgene competes with the reaction with the salt of the dihydroxyaromatic compound to form bischloroformate.

High pH levels during the reaction also promote the formation of bischloroformate oligomers having degrees of polymerization of 3 and higher, wherein aromatic moieties are linked through carbonate groups. Under many conditions, the presence of substantial proportions of such oligomers is not favored. This is especially true when conversion to cyclic polycarbonate oligomers is desired.

More recently, low pH methods of bischloroformate preparation have been developed in which the degree of oligomerization is substantially lower. Reference is made, for example, to U.S. Pat. No. 4,638,077 and copending, commonly owned application Ser. No. 871,984, filed Jun. 9, 1986. The bischloroformate compositions typically produced thereby comprise principally monomeric and dimeric bischloroformate. Also, relatively low phosgene levels, typically up to about 2.5 moles per mole of dihydroxyaromatic compound, are required.

Even in these low pH methods involving relatively small amounts of phosgene, it is generally found that some phosgene remains unreacted and must be removed during product recovery. Such removal procedures as purging with an inert gas followed by hydrolysis are inconvenient and require costly specialized equipment. Moreover, substantial proportions of monochloroformates, which are not as desirable as bischloroformates for use as intermediates, are frequently formed as by-products.

The present invention provides a simple method for removal of unreacted phosgene from bischloroformate compositions. Said method is inexpensive and can be conducted in normal reaction equipment. Moreover, the method provides additional benefits by converting by-product monochloroformates to bischloroformates, but does not substantially increase the proportion of bischloroformate oligomers in the composition.

The invention is an improvement in a method for preparing aromatic bischloroformate compositions which comprises reacting a dihydroxyaromatic compound with phosgene in the presence of an aqueous alkali or alkaline earth metal base and at least one substantially inert and substantially water-insoluble organic liquid at a pH below about 8. Said improvement comprises raising the pH of the aqueous phase to a higher value in the range of about 7–12 after all solid dihydroxyaromatic compound has been consumed, and maintaining it in said range until a major proportion of the unreacted phosgene has been hydrolyzed.

The dihydroxyaromatic compounds useful in the method of this invention generally have the formula $$HO-R-OH, \qquad (I)$$

wherein R is an aromatic hydrocarbon or substituted aromatic hydrocarbon radical. Illustrative substituents are alkyl, cycloalkyl, alkenyl (e.g., crosslinkable-graftable moieties such as vinyl and allyl), halo (especially fluoro, chloro and/or bromo), nitro and alkoxy.

The preferred dihydroxyaromatic compounds have the formula $$HO-A^1-Y-A^2-OH, \qquad (II)$$

wherein each of $A^1$ and $A^2$ is a single-ring divalent aromatic radical and Y is a bridging radical in which one or two atoms separate $A^1$ from $A^2$. The free valence bonds in formula II are usually in the meta or para positions of $A^1$ and $A^2$ in relation to Y. In formula II, the $A^1$ and $A^2$ values may be unsubstituted phenylene or substituted derivatives thereof wherein the substituents are as defined for R. Unsubstituted phenylene radicals are preferred. Both $A^1$ and $A^2$ are preferably p-phenylene, although both may be o- or m-phenylene or one o- or m-phenylene and the other p-phenylene.

The bridging radical, Y, is one in which one or two atoms, preferably one, separate $A^1$ from $A^2$. It is most often a hydrocarbon radical and particularly a saturated $C_{1-12}$ aliphatic or alicyclic radical such as methylene, cyclohexylmethylene, 2-[2.2.1]bicycloheptylmethylene, ethylene, ethylidene, 2,2-propylidene, 1,1-(2,2-dimethylpropylidene), cyclohexylidene, cyclopentadecylidene, cyclododecylidene or 2,2-adamantylidene, especially an alkylidene radical. Aryl-substituted radicals are included, as are unsaturated radicals and radicals containing atoms other than carbon and hydrogen, e.g., oxy groups. Substituents such as those previously enumerated may be present on the aliphatic, alicyclic and aromatic portions of the Y group. For reasons of availability and particular suitability for the purposes of this invention, the preferred radical of formula II is the 2,2-bis(4-phenylene)propane radical, which is derived from bisphenol A and in which Y is 2,2-propylidene and $A^1$ and $A^2$ are each p-phenylene.

For the most part, the suitable compounds include biphenols and especially bisphenols. Frequent reference will be made to bisphenols hereinafter, but it should be understood that other compounds equivalent thereto may be employed as appropriate.

The following dihydroxyaromatic compounds are illustrative:

Resorcinol
4-Bromoresorcinol
Hydroquinone
4,4'-Dihydroxybiphenyl
1,6-Dihydroxynaphthalene
2,6-Dihydroxynaphthalene
Bis(4-hydroxyphenyl)methane
Bis(4-hydroxyphenyl)diphenylmethane
Bis(4-hydroxyphenyl)-1-naphthylmethane
1,1-Bis(4-hydroxyphenyl)ethane
1,2-Bis(4-hydroxyphenyl)ethane
1,1-Bis(4-hydroxyphenyl)-1-phenylethane
2,2-Bis(4-hydroxyphenyl)propane ("bisphenol A")
2-(4-Hydroxyphenyl)-2-3-hydroxyphenyl) propane
2,2-Bis(4-hydroxyphenyl)butane
1,1-Bis(4-hydroxyphenyl)isobutane
1,1-Bis(4-hydroxyphenyl)cyclohexane
1,1-Bis(4-hydroxyphenyl)cyclododecane
Trans-2,3-bis(4-hydroxyphenyl)-2-butene
2,2-Bis(4-hydroxyphenyl)adamantane
α,α'-Bis(4-hydroxyphenyl)toluene
Bis(4-hydroxyphenyl)acetonitrile
2,2-Bis(3-methyl-4-hydroxyphenyl)propane
2,2-Bis(3-ethyl-4-hydroxyphenyl)propane
2,2-Bis(3-n-propyl-4-hydroxyphenyl)propane
2,2-Bis(3-isopropyl-4-hydroxyphenyl)propane
2,2-Bis(3-sec-butyl-4-hydroxyphenyl)propane
2,2-Bis(3-t-butyl-4-hydroxyphenyl)propane
2,2-Bis(3-cyclohexyl-4-hydroxyphenyl)propane
2,2-Bis(3-allyl-4-hydroxyphenyl)propane
2,2-Bis(3-methoxy-4-hydroxyphenyl)propane
2,2-Bis(3,5-dimethyl-4-hydroxyphenyl)propane
2,2-Bis(2,3,5,6-tetramethyl-4-hydroxyphenyl)propane
2,2-Bis(3-5-dichloro-4-hydroxyphenyl)propane
2,2-Bis(3,5-dibromo-4-hydroxyphenyl)propane
2,2-Bis(2,6-dibromo-3,5-dimethyl-4-hydroxyphenyl)propane
α,α-Bis(4-hydroxyphenyl)toluene
α,α,α',α'-Tetramethyl-α,α'-bis(4-hydroxyphenyl)-p-xylene
2,2-Bis(4-hydroxyphenyl)hexafluoropropane
1,1-Dichloro-2,2-bis(4-hydroxyphenyl)ethylene
1,1-Dibromo-2,2-bis(4-hydroxyphenyl)ethylene
1,1-Dichloro-2,2-bis(5-phenoxy-4-hydroxyphenyl)ethylene
4,4'-Dihydroxybenzophenone
3,3-Bis(4-hydroxyphenyl)-2-butanone
1,6-Bis(4-hydroxyphenyl)-1,6-hexanedione
Bis(4-hydroxyphenyl) ether
Bis(4-hydroxyphenyl) sulfide
Bis(4-hydroxyphenyl) sulfoxide
Bis(4-hydroxyphenyl) sulfone
Bis(3,5-dimethyl-4-hydroxyphenyl) sulfone
9,9-Bis(4-hydroxyphenyl)fluorene
2,7-Dihydroxypyrene
6,6'-Dihydroxy-3,3,3',3'-tetramethylspiro (bis)indane ("spirobiindane bisphenol")
3,3-Bis(4-hydroxyphenyl)phthalide
2,6-Dihydroxydibenzo-p-dioxin
2,6-Dihydroxythianthrene
2,7-Dihydroxyphenoxathiin
2,7-Dihydroxy-9,10-dimethylphenazine
3,6-Dihydroxydibenzofuran
3,6-Dihydroxydibenzothiophene
2,7-Dihydroxycarbazole.

The preferred dihydroxyaromatic compounds are those which are substantially insoluble in aqueous systems at temperatures within the range of 20°-40° C. and pH values in the range of about 2-5. Thus, dihydroxyaromatic compounds of relatively low molecular weight and high solubility in water, such as resorcinol and hydroquinone, are generally less preferred. Bisphenol A is often especially preferred for reasons of availability and particular suitability for the purposes of the invention.

The aqueous alkali or alkaline earth metal base is most often a hydroxide such as sodium hydroxide, potassium hydroxide or calcium hydroxide. Sodium and potassium hydroxides, and especially sodium hydroxide, are preferred because of their relative availability and low cost. The concentration of the aqueous base is not critical; about 1-16 M is typical.

Illustrative substantially inert organic liquids are aliphatic hydrocarbons such as hexane and n-heptane; chlorinated aliphatic hydrocarbons such as methylene chloride, chloroform, carbon tetrachloride, dichloroethane, trichloroethane, tetrachloroethane, dichloropropane and 1,2-dichloroethylene; aromatic hydrocarbons such as benzene, toluene and xylene; substituted aromatic hydrocarbons such as chlorobenzene, o-dichlorobenzene, the chlorotoluenes, nitrobenzene and acetophenone; and carbon disulfide. The chlorinated aliphatic hydrocarbons, especially methylene chloride, are preferred.

The invention is applicable under any circumstances involving reaction between the dihydroxyaromatic compound and phosgene at a pH below about 8. This is true regardless of the precise conditions of the reaction. For example, the procedure described in the aforementioned U.S. Pat. No. 4,638,077 requires passage of the phosgene and addition of the aqueous base into a heterogeneous mixture of the organic liquid and the bisphenol. On the other hand, the aforementioned copending application Ser. No. 871,984 discloses concurrent feeding to a back-mixed reactor of bisphenol, phosgene, organic liquid and aqueous base. The disclosures of said applications are incorporated by reference herein.

In procedures such as these which take place under these relatively low pH conditions, the major proportion of the bisphenol will exist as undissolved solid by reason of its relatively low solubility in water and the organic liquid. Dissolution in said liquid is the rate determining step in the process, since dissolved bisphenol quickly reacts with phosgene to form bischloroformate or monochloroformate, whereupon more bisphenol is free to dissolve until the entire portion thereof has dissolved and reacted. Thus, disappearance of solid bisphenol is an indication that the reaction is essentially complete.

It is at this point that the present invention comes into play. After all solid bisphenol has been consumed, the pH of the aqueous phase is raised to a value higher than that in the earlier step and in the range of about 7-12. This is typically achieved by the addition of further aqueous base.

It will immediately be apparent that the pH in both steps may be in the range of about 7-8. In that event, however, the pH is higher in the second step than in the first.

The principal effect of raising the pH is to provide conditions under which any remaining phosgene is rapidly decomposed to sodium chloride and carbon dioxide. Since essentially all the bisphenol has reacted, phosgene decomposition is not effectively in competition with bischloroformate formation. Moreover, it has unexpectedly been discovered that neither decomposition nor oligomerization of bischloroformate occurs to a substantial extent under these conditions.

The preferred pH range is about 9–11. This is true because such conditions are favorable for conversion of the free phenolic group in any monochloroformate by-product to phenoxide which then reacts preferentially with any phosgene or chloroformate groups present, yielding additional bischloroformate monomer or oligomer.

The distributions of the molecular species in the bischloroformate compositions prepared by the method of this invention may be determined by reversed phase high pressure liquid-liquid chromatography. The composition is first reacted with an equimolar mixture of phenol and triethylamine to produce the corresponding phenyl esters, which are resistant to hydrolysis under chromatography conditions. The phenyl esters are dissolved in a mixture of tetrahydrofuran and water and chromatographed using a relatively non-polar packing, whereupon lower molecular weight constituents are eluted first. For each molecular species, two values are determined and used for identification: the retention time (in minutes) and the area under the ultraviolet absorption peak at 254 nm., which is uniquely identifiable for compounds of this type.

The standards used for assignment of retention time and 254 nm. absorption are separately prepared linear compounds including diphenyl carbonate (obtained from unreacted phosgene), bisphenol A mono- and diphenyl carbonate and the diphenyl carbonate of bisphenol A dimer. Higher oligomers are detected by analogy.

The invention is illustrated by the following examples.

EXAMPLE 1

A round-bottomed flask fitted with a phosgene addition tube, stirrer and solid carbon dioxide-filled condenser was charged with 22.8 grams (100 mmol.) of bisphenol A, 150 ml. of methylene chloride and 200 mg. of benzophenone as an internal standard. Phosgene, 21.8 grams (220 mmol.), was passed in at 2 grams per minute, with stirring. The pH of the aqueous phase was maintained in the range of 2–5 by addition of 10% aqueous sodium hydroxide solution. When all of the solid bisphenol A had disappeared, the pH was raised to 7–8 by further addition of base and maintained in that range over several minutes. Several samples were removed, quenched with aqueous hydrochloric acid solution and reacted with excess phenol and triethylamine in methylene chloride at 0°. The products were analyzed for diphenyl carbonate (formed from unreacted phosgene) by high pressure liquid chromatography.

The results are listed in Table I. Unreacted phosgene concentration is measured in units corresponding to the relative area under the chromatography curve as compared to the internal standard. With respect to proportions of chloroformates, no substantial change was noted over the reaction time employed.

TABLE I

| Reaction time, min. | Unreacted phosgene remaining |
| --- | --- |
| 0 | 1.87 |
| 2 | 0.96 |
| 5 | 0.35 |
| 10 | 0.03 |

EXAMPLE 2

The procedure of Example 1 was repeated, except that the pH after completion of the reaction was maintained in the range of 10–11 by the addition of larger amounts of aqueous base. The rate of phosgene decomposition was similar to that of Example 1. The proportions of chloroformate species in the product immediately upon raising the pH and after 10 minutes are listed in Table II.

TABLE II

| | % by weight | |
| --- | --- | --- |
| | 0 min. | 10 min. |
| Monomer monochloroformate | 7.8 | 0 |
| Monomer bischloroformate | 42.3 | 55.3 |
| Dimer monochloroformate | 7.1 | 0 |
| Dimer bischloroformate | 21.7 | 24.2 |
| Trimer bischloroformate | 11.7 | 12.8 |
| Tetramer bischloroformate | 6.6 | 6.5 |
| Pentamer bischloroformate | 2.8 | 1.3 |

What is claimed is:

1. In a method for preparing aromatic bischloroformate compositions which comprises reacting a dihydroxyaromatic compound with phosgene in the presence of an aqueous alkali or alkaline earth metal base and at least one substantially inert and substantially water-insoluble organic liquid at a pH below about 8, the improvement which comprises raising the pH of the aqueous phase to a higher value in the range of about 7–12 after all solid dihydroxyaromatic compound has been consumed, and maintaining it in said range until a major proportion of the unreacted phosgene has been hydrolyzed.

2. A method according to claim 1 wherein the dihydroxyaromatic compound has the formula $$HO-A^1-Y-A^2-OH, \qquad (II)$$

wherein each of $A^1$ and $A^2$ is a single-ring divalent aromatic radical and Y is a bridging radical in which 1 or 2 atoms separate $A^1$ from $A^2$.

3. A method according to claim 2 wherein the pH is raised by the addition of further aqueous base.

4. A method according to claim 3 wherein the base is sodium hydroxide.

5. A method according to claim 4 wherein the organic liquid is methylene chloride.

6. A method according to claim 5 wherein the dihydroxyaromatic compound is bisphenol A.

7. In a method for preparing aromatic bischloroformate compositions which comprises reacting a dihydroxyaromatic compound with phosgene in the presence of an aqueous alkali or alkaline earth metal base and at least one substantially inert and substantially water-insoluble organic liquid at a pH bbelow about 8, the improvement which comprises raising the pH of the aqueous phase to a higher value in the range of about 9–11 after all solid dihydroxyaromatic compound has been consumed, and maintaining it in said range until a major proportion of the unreacted phosgene has been hydrolyzed.

8. A method according to claim 7 wherein the dihydroxyaromatic compound has the formula $$HO-A^1-Y-A^2-OH, \qquad (II)$$

wherein each of $A^1$ and $A^2$ is a single-ring divalent aromatic radical and Y is a bridging radical in which 1 or 2 atoms separate $A^1$ from $A^2$.

9. A method according to claim 8 wherein the pH is raised by the addition of further aqueous base.

10. A method according to claim 9 wherein the base is sodium hydroxide.

11. A method according to claim 10 wherein the organic liquid is methylene chloride.

12. A method according to claim 11 wherein the dihydroxyaromatic compound is bisphenol A.

* * * * *